(12) United States Patent
Chin et al.

(10) Patent No.: US 6,225,528 B1
(45) Date of Patent: May 1, 2001

(54) METHOD OF MAKING PATHOGEN-RESISTANT PLANTS BY TRANSFORMATION WITH A FATTY ACID DESATURASE GENE

(75) Inventors: Chee-Kok Chin, Holmdel; Chunlin Wang, Piscataway; Jinsong Xing, New Brunswick, all of NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/143,567

(22) Filed: Aug. 28, 1998

Related U.S. Application Data

(60) Provisional application No. 60/057,510, filed on Sep. 4, 1997.

(51) Int. Cl.[7] ................................................ C12N 15/82
(52) U.S. Cl. .............................................................. 800/279
(58) Field of Search ........................... 536/23.2, 23.74; 435/69.1, 320.1, 419, 468; 800/279, 281, 301, 317, 317.3, 317.4

(56) References Cited

PUBLICATIONS

Stam M, et al. "The silence of genes in transgenic plants." Ann. Bot. 79: 3–12, 1997.*

Koziel MG, et al. "Optimizing expression of transgenes with an emphasis on post–transcriptional events." Plant Mol. Biol. 32: 393–405, 1996.*

Smith CJS, et al. "Antisense RNA inhibition of polygalacturonase gene expression in transgenic tomatoes." Nature 334: 724–726, Aug. 25, 1988.*

Cohen et al., 1991, Physiological and Molecular Plant Pathology 38: 255–263.

Polashok et al., 1992, Plant Physiol. 100: 894–901.

Wang et al., 1996, J. Agric. Food Chem. 44: 3399–3402.

* cited by examiner

*Primary Examiner*—Amy J. Nelson
(74) *Attorney, Agent, or Firm*—Janet E. Reed; Saul Ewing LLP

(57) ABSTRACT

The present invention provides pathogen-resistant transgenic plants and methods of making the plants. The transgenic plants display enhanced resistance to a variety of fungal, bacterial and viral plant pathogens due to expression of a gene that increases the unsaturated fatty acid content of the plant's cells, as compared with an equivalent, but non-transformed plant. The preferred embodiment of the invention is a plant expressing a heterologous Δ-9 desaturase gene from yeast, which particularly increases cytosolic quantities of 16:1, 16:2 and 18:1 fatty acids.

7 Claims, 9 Drawing Sheets

Figure 2A:
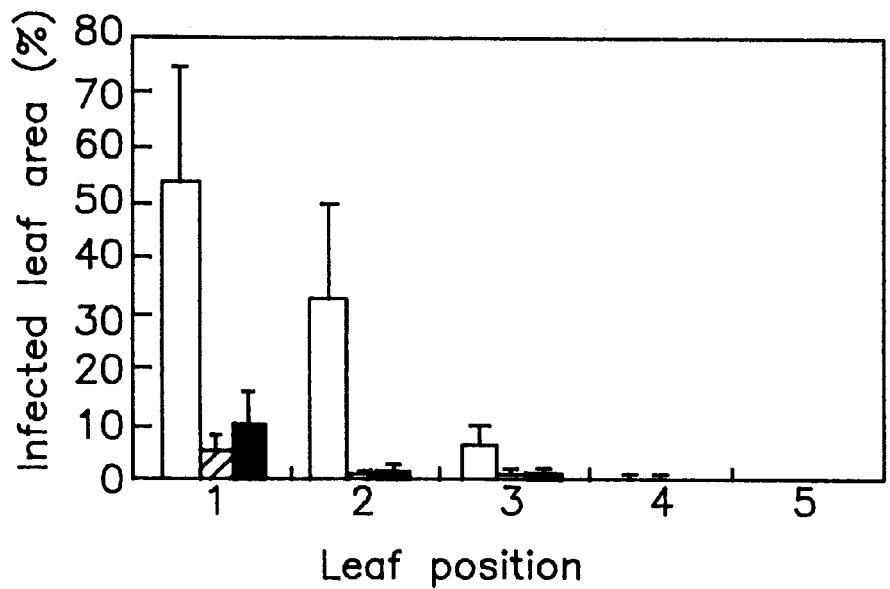

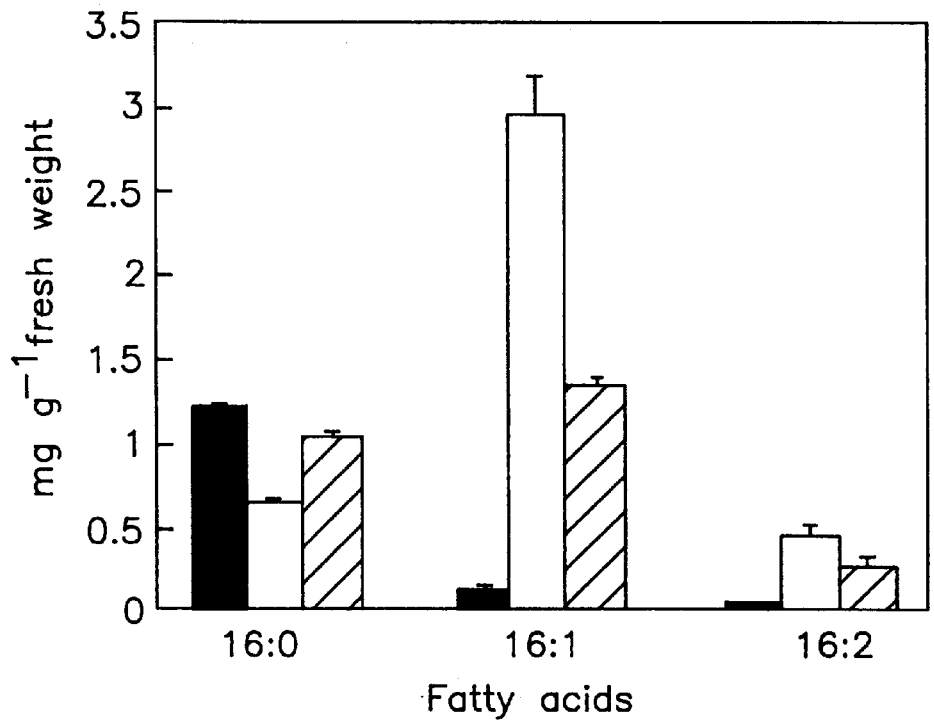
FIG. IA
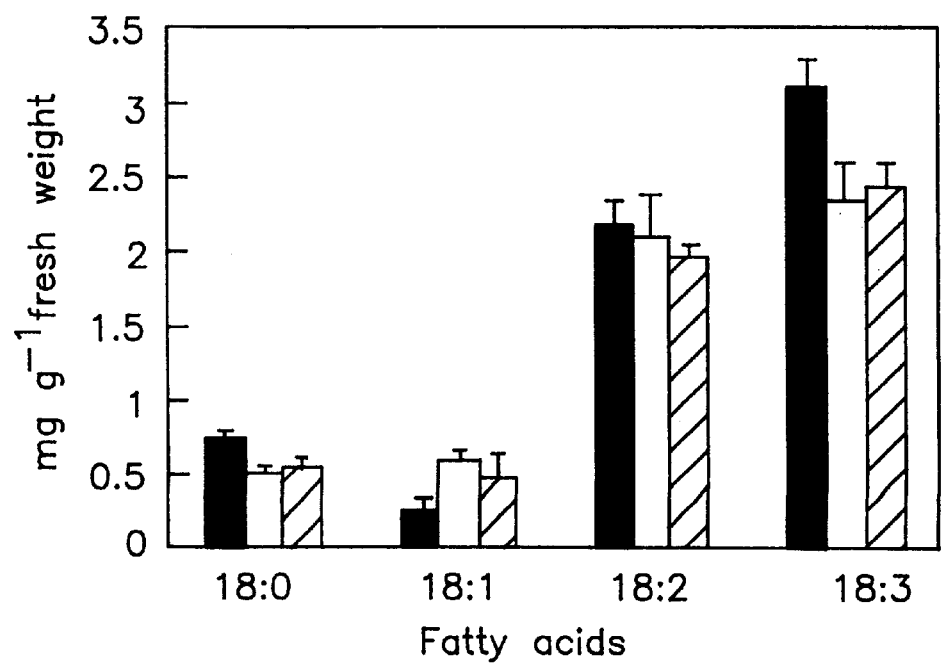
FIG. IB

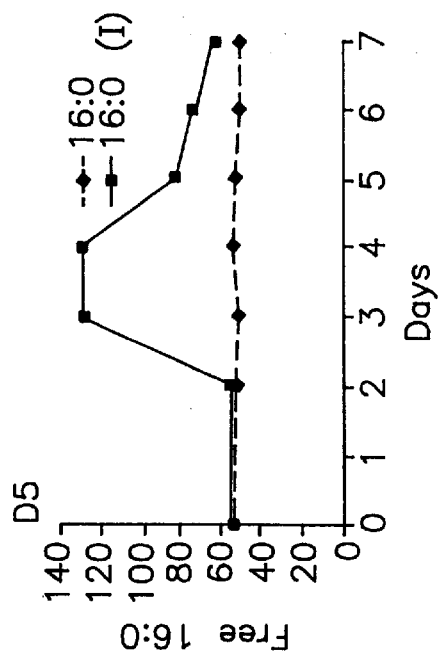
FIG. IOB
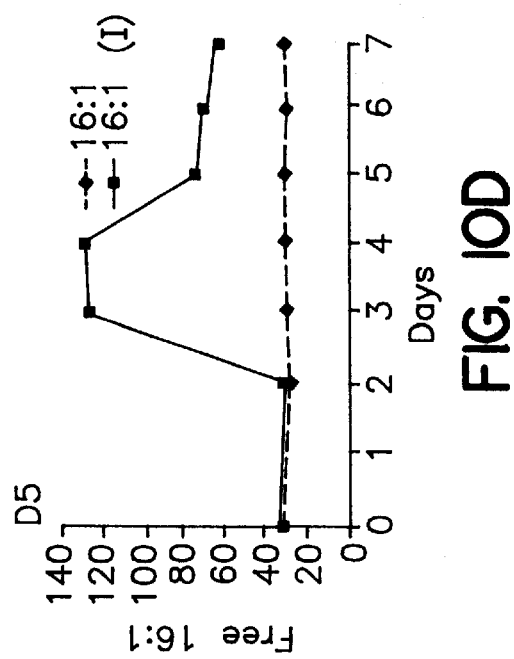
FIG. IOD
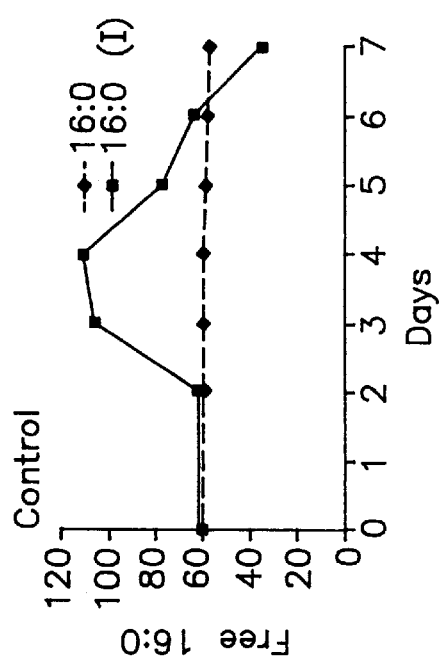
FIG. IOA
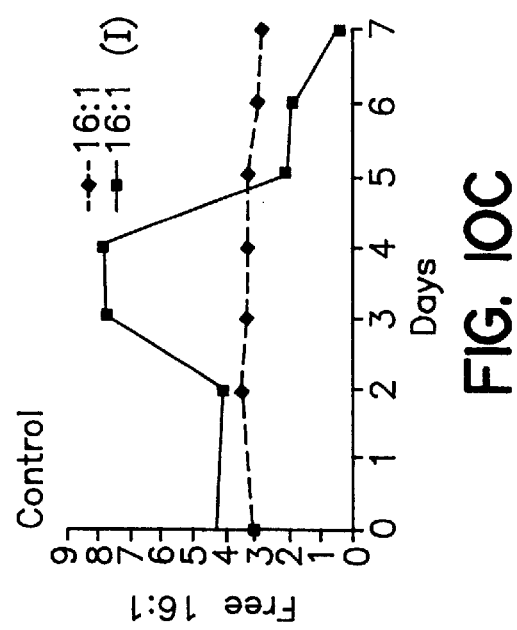
FIG. IOC

US 6,225,528 B1

METHOD OF MAKING PATHOGEN-RESISTANT PLANTS BY TRANSFORMATION WITH A FATTY ACID DESATURASE GENE

This application claims priority to U.S. Provisional Application No. 60/057,510, filed Sep. 4, 1997, which is incorporated by reference herein.

FIELD OF THE INVENTION

This invention relates to the field of plant pathology and plant genetic transformation. In particular, the invention provides a method for producing transgenic plants having increased resistance to a wide variety of plant pathogens.

BACKGROUND OF THE INVENTION

Several publications are referenced throughout the specification to describe the state of the art to which this invention pertains. These publications are incorporated by reference herein.

Plant disease is a major cause of crop loss. Various strategies have been developed to control disease, one of the most common of which is the use of chemicals. This approach is usually expensive, not always effective, and often harmful to humans and the environment. A preferred approach is to develop, through breeding, genotypes resistant to diseases.

Conventional plant breeding has been based on genetic recombination through sexual crosses. Although nearly all of the current improved plants are developed through conventional breeding techniques, there are limitations to this approach. These include the lack of availability of appropriate germplasm and the incompatibility of certain crosses.

With the recent advances in molecular biology and gene transfer technology for plants, it has become possible to circumvent some of the limitations of conventional breeding by obtaining genes of interest from diverse sources and introducing them into crop plants by genetic transformation. Methods are now available in the art for transforming a wide variety of plant species, including both monocotyledonous and dicotyledonous flowering plants, which contain nearly all agronomically and horticulturally important crops.

The microbial causal agents of plant disease include fungi, bacteria and viruses. Plants have active mechanisms for defending themselves against microbial pathogen infection. For most resistant plants, challenge by a pathogen results in induction of a dual defense mechanisms, part of which is located at the site of infection, occurring as necrotic lesions resulting from host cell death (hypersensitive responses). Another part of the defense occurs in the surrounding, and even distal, uninfected parts of the plant (systemic acquired resistance). The HR is a highly regulated process involving cellular protein synthesis, increased cytosolic calcium ion levels, generation of reactive oxygen species, alteration of protein phosphorylation, among other signal responses. Both the hypersensitive response and systemic acquired resistance are associated with activated expression of a large number of defense or defense-related genes (such as PR genes), some of whose products may play important roles in the restriction of pathogen proliferation and spread by participating in strengthening host cellular structures or through their direct antimicrobial activities.

Salicylic acid has been identified as an important signalling factor in the induction of plant disease resistance. Evidence indicates that a systemic increase in salicylic acid is important for the induction of systemic acquired resistance. Salicylic acid also appears to play an important role in the primary, local defense associated with the hypersensitive cell death. One proposed mechanism of action of salicylic acid is to inhibit catalase activity, thereby elevating $H_2O_2$ levels. These elevated levels of $H_2O_2$ or other reactive oxygen species derived from $H_2O_2$ may serve as a signal for activation of plant defenses such as the synthesis of PR proteins (Chen et al., 1993, Science 262: 1883–1886).

In some resistance responses, plants challenged with a pathogen produce their own anti-microbial substances, termed "phytoalexins." The production of phytoalexins in the resistance response has been well characterized in several species. For instance, localized and systemic resistance of certain potato varieties to *Phytophthora infestans* may be elicited by several substances, including various portions of the fungus itself, and certain long-chain polyunsaturated fatty acids, such as arachidonic and eicosopentanoic acids. Systemic resistance of potato plants to *P. infestans* following surface applications of long-chain polyunsaturated fatty acids, eicosopentanoic (20:5), arachidonic (20:4), linolenic (18:3) and linoleic (18:2), has been reported (Cohen et al., 1991, Physiological and Molecular Plant Pathology 38: 255–263). However, systemic resistance was directly correlated with phytotoxicity of the fatty acids tested (oleic acid (18:1) was found to be neither phytotoxic nor an inducer of systemic resistance). Thus, it would appear from this report that long-chain polyunsaturated fatty acids are unsuitable for purposes of eliciting pathogen resistance in plants, due to phytotoxicity.

In plants, fatty acids are first produced in saturated forms. They are subsequently desaturated by a series of desaturases, the first of which is a Δ-9 desaturase that produces monounsaturated fatty acids. Further desaturation results in the formation of polyunsaturated fatty acids. A Δ-9 desaturase from yeast has been expressed in tobacco (Polashok et al., 1992, Plant Physiol. 100: 894–901) and tomato (Wang et al., 1996, J. Agric. Food Chem. 44: 3399–3402). Expression of yeast desaturase was reported to alter the fatty acid composition of both plants (increasing 16:1 and 18:1 monounsaturated fatty acids, as well as certain polyunsaturated fatty acids), with no apparent alteration in phenotype. However, no reference has been made to the relative pathogen resistance of the yeast desaturase-transgenic plants, as compared to non-transformed plants.

SUMMARY OF THE INVENTION

Surprisingly, it has now been discovered that transgenic plants expressing genes that lead to increased production of unsaturated fatty acids with no apparent phenotypic abnormalities also exhibit resistance to a wide variety of plant pathogens, including fungi, bacteria and viruses. Thus, according to one aspect of the present invention, a method is provided for making a pathogen-resistant plant, which comprises (1) transforming regenerable cells of the plant with a heterologous DNA, expressible in a plant, encoding an enzyme whose activity increases production of at least one unsaturated fatty acid; and (2) regenerating a transgenic plant from the cells which produces more unsaturated fatty acid than its untransformed counterpart, the production of the fatty acid causing the plant to be pathogen-resistant.

In a preferred embodiment of the invention, the transgenic plant comprises and expresses a DNA molecule encoding a Δ-9 desaturase enzyme. Most preferably, the enzyme is a yeast Δ-9 desaturase. In other embodiments, the transgenic plant comprises and expresses one or more DNA molecules encoding other desaturases, including, but not limited to (1) mammalian desaturases such as Δ-4, Δ-5 and Δ-6 desaturase; (2) plant desaturases such as Δ-9, Δ-15 (omega-6) and Δ-15 (omega-3); and (3) related fatty acid desaturases from other organisms, such as fish. Desaturases of non-plant origin may be modified for expression in plants, according to standard methods.

According to another aspect of the invention, transgenic plants produced by the foregoing methods are provided. In preferred embodiments, the plants are selected from the group consisting of tobacco, tomato and eggplant.

According to another aspect of the invention, the aforementioned method, and the transgenic plants produced by the method, further comprises transforming the plant with an expressible DNA encoding an enzyme selected from the group consisting of lipases and lipoxygenases. Preferably, the lipase is phospholipase $A_2$.

Other features and advantages of the present invention will be understood by reference to the drawings, detailed description and examples that follow.

BRIEF DESCRIPTION OP THE DRAWINGS

FIG. 1. Fatty acids levels in control and transgenic tomato leaves. Top young leaves were used. Data represent means of 3 replications, each with 5 plants for each genotype. Black bars=untransformed control plants; white bars=transformed T4 line; hatched bars=transformed T5 line.

FIG. 2. Powdery mildew development on control and transgenic tomato plants. Data represent means and standard deviations from three replications, each with 12 plants. White bars=untransformed control plants; hatched bars= transformed T4 line; black bars=transformed T5 line.

FIG. 3. Colony size and number of conidia per colony on control and transgenic tomato leaves. Data were taken 10 days after inoculation and represent means and standard deviations from 15 colonies. CK=untransformed control plants; T4=transformed T4 line; T5=transformed T5 line.

FIG. 4. The effects of various fatty acids on spore germination of *Erysiphe polygoni*. Data represent the averages of three replications. In each replication over 100 spores were counted.

Figure 5:
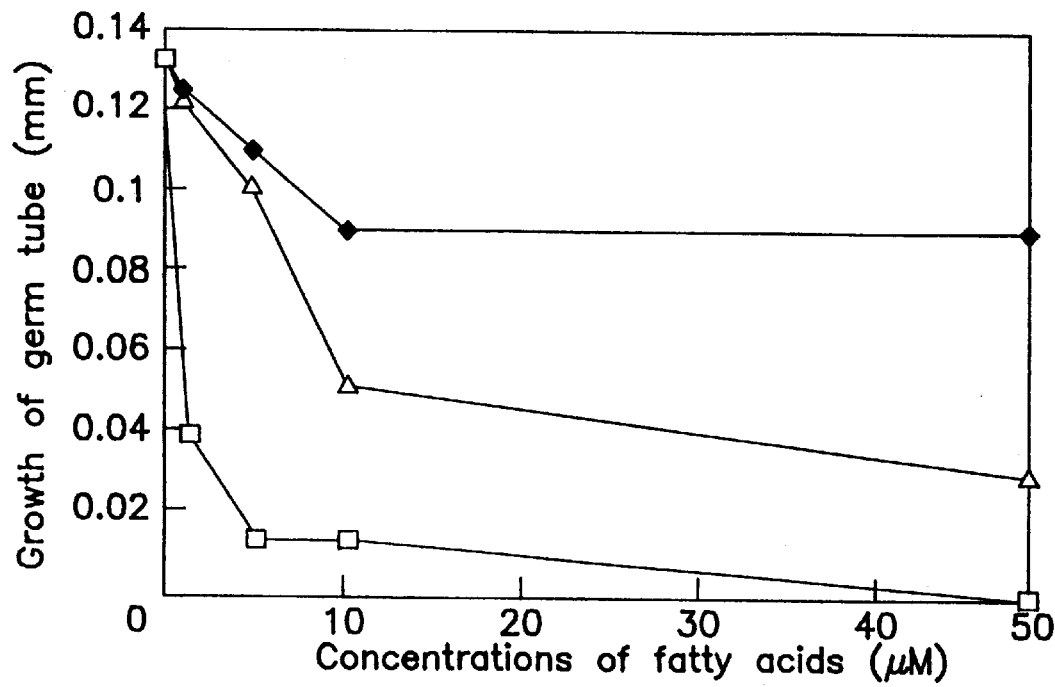

FIG. 5. The effects of fatty acids on germ tube elongation. Data were taken at the end of 12 hrs and represent the averages of at least 30 measurements.

Figure 6:
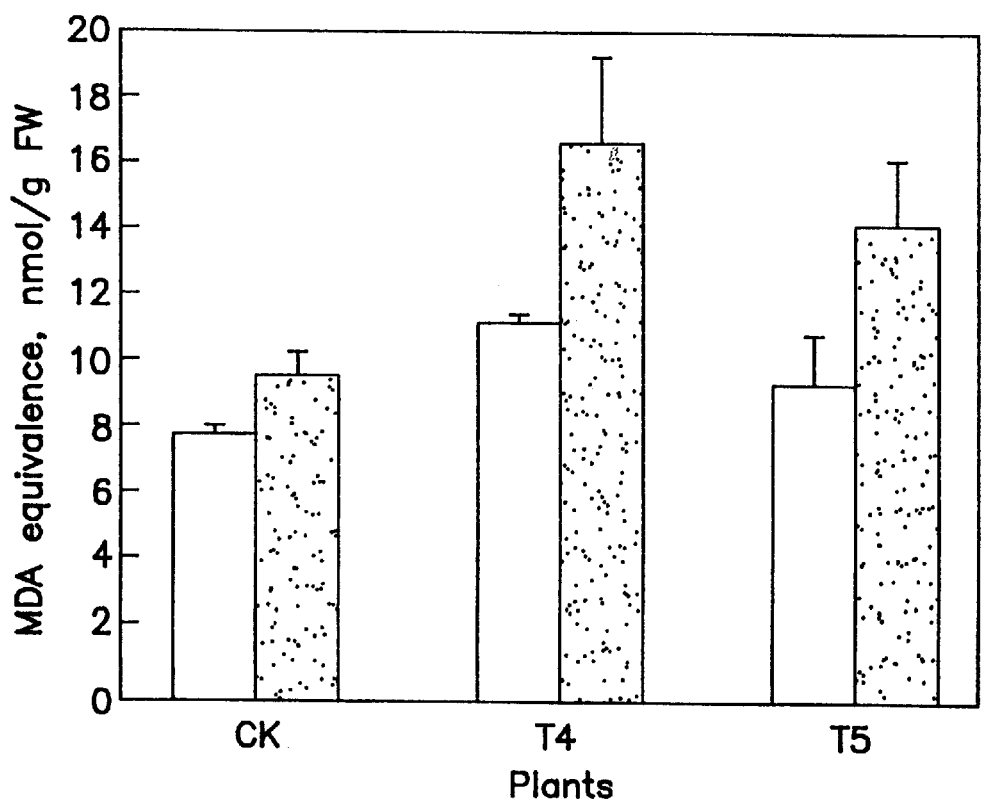

FIG. 6. Production of lipid peroxides expressed as malondialdehyde equivalence from thiobarbituric acid test. The third fully expanded leaves were inoculated and measured 10 days after. Data represent means and standard deviations from three replications. White bars represent plants not inoculated with *E. polygoni*; grey bars represent plants inoculated with *E. polygoni*; CK=untransformed control plants; T4=transformed T4 line; T5=transformed T5 line.

Figure 7:
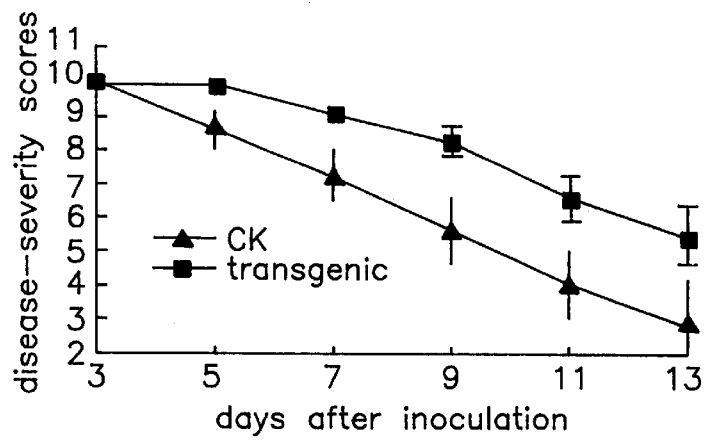

FIG. 7. Time course of disease severity following inoculation of transgenic and control eggplants with *Verticillium dahliae* (triangles=control plants (CK); squares=transgenic plants).

Figure 8:
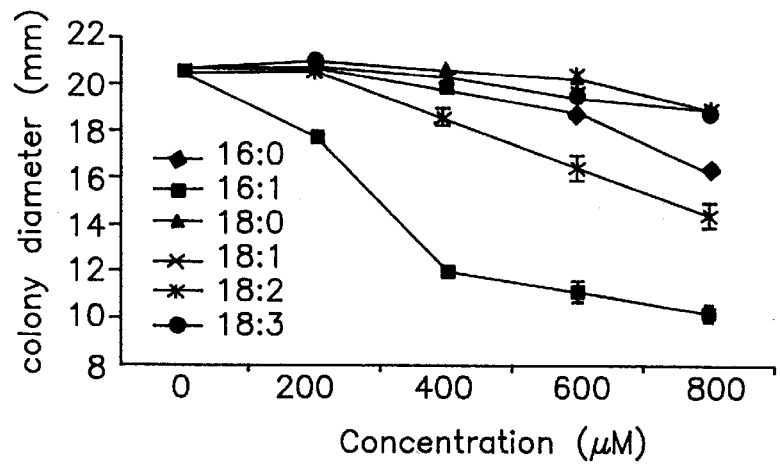

FIG. 8. Inhibitory effect of various fatty acids on Verticillium colony size in vitro.

Figure 9:
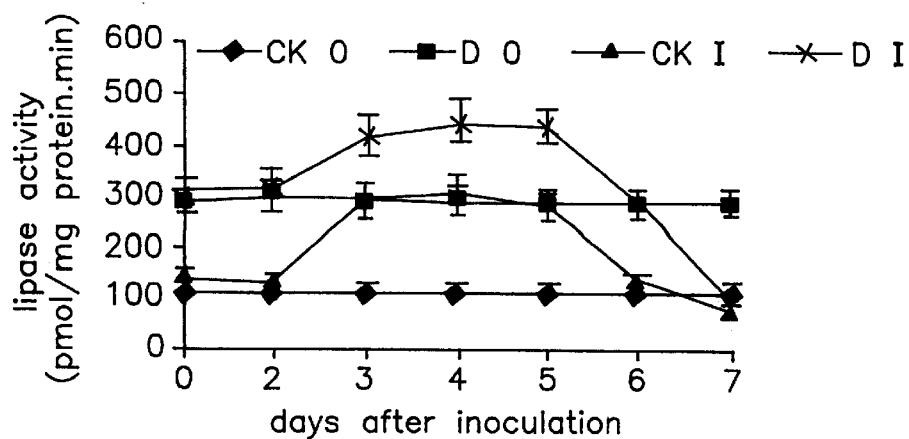

FIG. 9. Time course of phospholipase $A_2$ activity in eggplants after inoculation of plants with *Verticillium dahliae*. CK 0=uninoculated control plants; D 0=uninoculated transgenic plants; CK I inoculated control plants; D I=inoculated transgenic plants.

FIG. 10. Time course of changes in 16:0 and 16:1 free fatty acid content of eggplant cells following inoculation of plants with *Verticillium dahliae*.

FIG. 10A—free 16:0 in control plants;

FIG. 10B—Free 16:0 in transgenic plants;

FIG. 10C—Free 16:1 in control plants;

FIG. 10D—Free 16:1 in transgenic plants. Squares= inoculated plants; diamonds=uninoculated plants.

Figure 11:
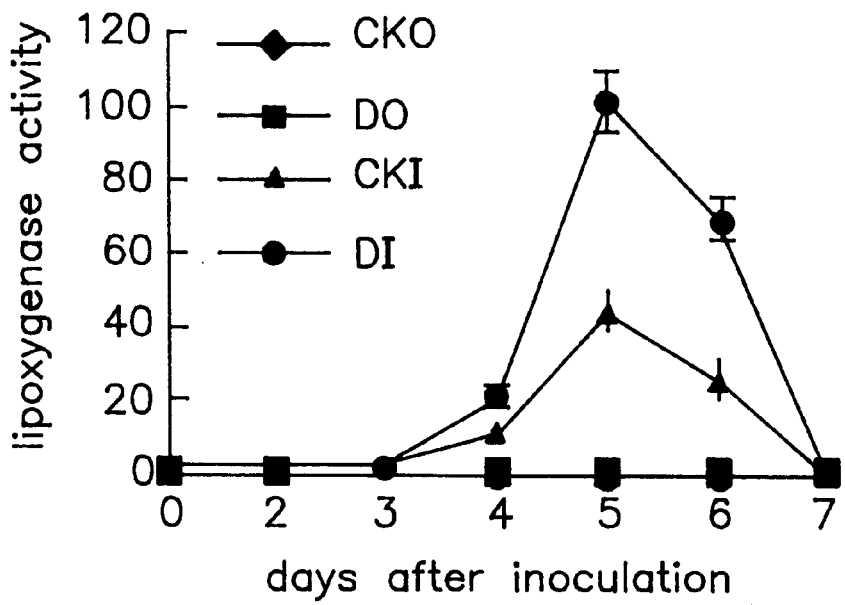

FIG. 11. Time course of lipoxygenase activity (pkatal/ug protein) following inoculation of eggplants with *Verticillium dahliae* (CK 0=uninoculated control, CK I=inoculated control, D 0=uninoculated transgenic, D I=inoculated transgenic).

Figure 12:
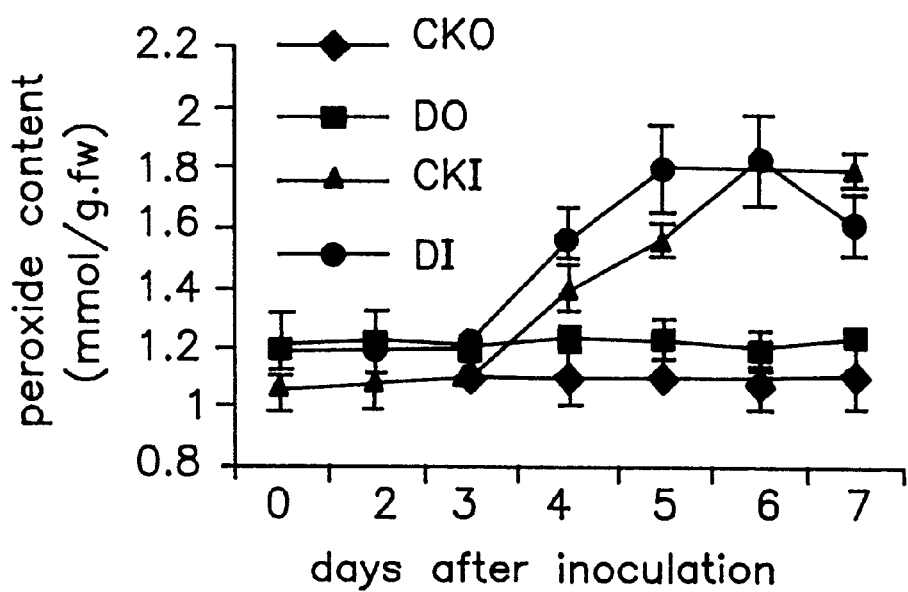

FIG. 12. Time course of lipid peroxide accumulation following inoculation of eggplants with *Verticillium dahliae* (CK 0=uninoculated control, CK I=inoculated control, D 0=uninoculated transgenic, D I=inoculated transgenic).

DETAILED DESCRIPTION OF THE INVENTION

I. Definitions

Various terms relating to the methods and compositions of the present invention are used throughout the specification and claims.

The term "ectopic expression" refers to a pattern of subcellular, cell-type, tissue-type and/or developmental or temporal (e.g., light/dark) expression that is not normal for the particular gene or enzyme in question. It also refers to expression of a heterologous gene; e.g. a gene not naturally occurring in the organism (also termed "transgene" as described below). Such ectopic expression does not necessarily exclude expression in normal tissues or developmental stages.

The term "overexpression" means a greater than normal expression level of a gene in the particular tissue, cell and/or developmental or temporal stage for the gene. Such overexpression results in "overproduction" of the enzyme encoded by the gene, which means a greater than normal production of the enzyme in a particular tissue or cell, or developmental or temporal stage for the enzyme.

The term "disease defense response" or "disease resistance response" refers to a change in metabolism, biosynthetic activity or gene expression that enhances the plant's ability to suppress the replication and spread of a microbial pathogen (i.e., to resist the microbial pathogen). Examples of plant disease defense responses include, but are not limited to, production of low molecular weight compounds with antimicrobial activity (referred to as phytoalexins) and induction of expression of defense (or defense-related) genes, whose products include, for example, peroxidases, cell wall proteins, proteinase inhibitors, hydrolytic enzymes, pathogenesis-related (PR) proteins and phytoalexin biosynthetic enzymes, such as phenylalanine ammonia lyase and chalcone synthase. Such defense responses appear to be induced in plants by several signal transduction pathways involving secondary defense signaling molecules produced in plants. Agents that induce disease defense responses in plants include, but are not limited to: (1) microbial pathogens, such as fungi, bacteria, viruses and nematodes; (2) microbial components and other defense response elicitors, such as proteins and protein fragments, small peptides, β-glucans, elicitins (a family of small extracellular proteins produced by the pathogenic fungal genus Phytophthora), harpins (a bacterial-encoded elicitor) and oligosaccharides; and (3) secondary defense signaling molecules produced by the plant, such as SA, $H_2O_2$, ethylene and jasmonates.

In this invention, the term "promoter" or "promoter region" refers to the transcriptional regulatory regions of a gene, including promoters per se (e.g., CaMV 35S promoters and/or tetracycline repressor/operator gene promoters), as well as other regulatory sequences, such as enhancers.

The term "5' regulatory region" is also used herein, to refer to promoters located 5' to the coding sequence, as well as translational regulatory sequences located on the 5' end of the coding sequence.

The term "selectable marker" refers to a gene product that confers a selectable phenotype, such as antibiotic resistance, on a transformed cell or plant. Selectable markers are encoded by expressible DNA sequences, which are sometimes referred to herein as "selectable marker genes."

The terms "operably linked", "operably inserted" or "operably associated" mean that the regulatory sequences necessary for expression of the coding sequences are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

The term "DNA construct" refers to genetic sequence used to transform plant cells and generate progeny transgenic plants. At minimum a DNA construct comprises a coding region for a selected gene product, operably linked to 5' and 3' regulatory sequences for expression in transformed plants. In preferred embodiments, such constructs are chimeric, i.e., the coding sequence is from a different source one or more of the regulatory sequences (e.g., coding sequence from tobacco and promoter from cauliflower mosaic virus). However, non-chimeric DNA constructs also can be used. DNA constructs may be administered to plants in a viral or plasmid vector. Other methods of delivery such as Agrobacterium T-DNA mediated transformation and transformation using the biolistic process are also contemplated to be within the scope of the present invention. The transforming DNA may be prepared according to standard protocols such as those set forth in Ausubel et al. (1998). A plant species or cultivar may be transformed with a DNA construct (chimeric or non-chimeric) that encodes a polypeptide from a different plant species or cultivar (e.g., poplar transformed with a gene encoding a pine protein). Alternatively, a plant species or cultivar may be transformed with a DNA construct (chimeric or non-chimeric) that encodes a polypeptide from the same plant species or cultivar. The term "transgene" is sometimes used to refer to the DNA construct within the transformed cell or plant.

II. Description

It has been discovered in accordance with the present invention that transgenic plants engineered to overproduce unsaturated fatty acids exhibit a disease resistance response upon challenge with a pathogenic microorganism. The discovery made in accordance with the invention is exemplified by transgenic plants expressing the yeast Δ-nine desaturase enzyme. The yeast Δ-9 desaturase enzyme is expressed in the cytosol, as compared with the plant native Δ-9 desaturase, which is expressed in the chloroplast. The yeast enzyme catalyzes the conversion of 16:0 and 18:0 fatty acids to 16:1 and 18:1 respectively, both of which are minor constituents of plant cells. An increase in related polyunsaturated fatty acids has also been observed in plants transformed with the yeast Δ-9 desaturase, presumably due to the activity of native plant desaturases.

Transformation with the yeast Δ-9 desaturase and resultant altered fatty acid composition has been demonstrated in tobacco, tomato and eggplant. Concomitant pathogen resistance has been demonstrated in tomato and eggplant. However, the discoveries made in accordance with the present invention are expected to be applicable to any higher plant, such that all plants are contemplated for use in this invention. These include herbaceous dicotyledonous and monocotyledonous angiosperms, woody angiosperms and gymnosperms.

Pathogens to which resistance has been demonstrated include fungi, such as *Erisyphe polygoni, Phytophthora capsicci, Verticillium dahliae* and other Verticillium spp., and Fusarium spp., bacteria, such as *Pseudomonas syringae* pv. tomato, and viruses, such as tobacco mosaic virus. The fact that the transgenic plants of the present invention are resistant to such a diverse range of pathogens indicates that resistance occurs via one or more general mechanisms, and is not microorganism-selective. Accordingly, this invention encompasses plants with enhanced resistance to fungi, bacteria and viruses of all types, as well as any other agent or organism that induces a disease defense response in plants.

An exemplary embodiment of the present invention comprises transgenic tomato (*Lycopersicon esculentum* Mill.) plants transformed with a yeast Δ-9 desaturase gene contained in an expression plasmid under regulation of strong constitutive CaMV 35S promoter. The yeast Δ-9 desaturase is described in detail in U.S. Pat. No. 5,057,419 to Martin et al., which is incorporated herein by reference, and the expression plasmid is described in Polashock et al., (1992) Plant Physiology 100: 894–901, also incorporated herein by reference. A yeast Δ-9 desaturase gene customized for expression in plants is described in commonly-owned, co-pending PCT Application No. US99/19443 to Martin et al., also incorporated by reference herein.

As described in greater detail in the examples to follow, expression of the yeast Δ-9 desaturase gene in tomato plants led to increased levels of 16:1, 16:2 and 18:1 fatty acids and concomitant improved resistance to powdery mildew. Without the present invention being limited by any hypothesis as to mechanism of action, the correlation between elevated unsaturated fatty acids and disease resistance could be due to one or more of several factors. As described in the examples, several unsaturated fatty acids were found to directly inhibit germination and germ tube elongation of fungal spores. Thus, elevated unsaturated fatty acids may inhibit pathogen invasion by retarding spore germination and growth.

Another mechanism is that the increased unsaturated fatty acid "pool" in the transgenic plants results in increased formation of lipid peroxides, e.g. via lipoxygenase (Hildebrand, 1989, Physiologia Plantarum 76: 249–253). Peroxides, including hydroperoxides, have been reported to function directly as anti-microbial substances (Lynch & Thompson, 1984, FEBS Lett. 173: 251–271; Mehdy, 1994, Plant Physiol. 105: 467–472). More significantly, lipid peroxides have been reported as signaling molecules leading to systemic acquired resistance via the salicylic acid-mediated signal transduction pathway (Durner & Klessig, 1996, J. Biol. Chem. 271: 28492–28501; Conrath et al., 1997, Plant J. 11: 747–757). By this mechanism, even a small increase in lipid peroxide concentration (such as could be caused by increasing the "pool" of suitable fatty acid substrates for peroxidation), could lead to induction of systemic resistance responses in the plant upon challenge by a disease-causing agent.

The results reported in Example 3 support and extend both of the aforementioned explanations as to mechanism of disease resistance in the transgenic plants. It is known that fatty acids are not generally found in cells in a free state, but rather are sequestered and incorporated into lipids. The inventors have determined that, especially with regard to the additional 16:1 made in transgenic plants, this fatty acid is incorporated predominantly into the second position of plant cellular lipids. Upon challenge with a pathogen (e.g., *Verticillium dahliae* on a susceptible variety of eggplant, as discussed in Example 3), an increase in phospholipase $A_2$ activity is observed. Phospholipase $A_2$ cleaves fatty acids from lipids in the second position. As a result, in transgenic plants expressing desaturases, such as the Δ-9 desaturase, the fatty acids liberated by the increased activity of phospholipase $A_2$ comprise a greater proportion of unsaturated fatty acids (especially 16:1) than do non-transgenic plants.

In the transgenic eggplants described in Example 3, phospholipase $A_2$ activity was constitutively higher in transgenic versus non-transgenic plants, and the activity was induced in both transgenic and non-transgenic plants shortly after inoculation with the pathogen. Similarly, the free unsaturated fatty acid content of transgenic plants was higher than in non-transgenic plants, but a free fatty acid burst was observed in both transgenic and non-transgenic plants coincidentally with the stimulation of phospholipase $A_2$ activity.

Lipoxygenase activity was also higher in transgenic versus non-transgenic plants, but was induced to elevated expression/activity in both transgenic and non-transgenic plants about one day after the free fatty acid increase was observed. Following this, an increased amount of lipid peroxides was observed in the plants, with a greater amount occurring in the transgenic plants.

Taken together, the foregoing experimental results indicate a disease response mechanism in plants comprising (1) induction of phospholipase $A_2$ (other lipases are also likely to be induced), (2) a free fatty acid burst, (3) induction of lipoxygenase, and (4) an increase in lipid peroxide content. In transgenic plants, the free fatty acids are comparatively more unsaturated, which may enhance disease resistance by one or more mechanisms, including (1) direct inhibition of fungal spore germination and hyphal growth, (2) production of antimicrobial compounds in a localized response (e.g., hydroperoxides, lipid peroxides), and (3) signaling a systemic response via lipid peroxides.

This invention provides transgenic plants exhibiting resistance to a variety of microbial pathogens by virtue of expressing a transgene that results in overproduction of certain fatty acids, e.g., 16:1, 16:2 and 18:1 (preferably 16:1). Furthermore, this resistance is expected to be further enhanced by overproduction of enzymes involved in the lipase/lipoxygenase disease resistance response described above. Accordingly, this invention encompasses transgenic plants that overproduce lipases, such as phospholipase $A_2$, and lipoxygenases via ectopic expression of genes encoding those enzymes. Lipase or lipoxygenase-overproducing transgenic plants may also express one or more of the desaturase enzymes mentioned above, but such is not required for this embodiment.

The present invention also is intended to encompass cells and tissues of the aforementioned transgenic plants, including, but not limited to, leaves, stems, shoots, roots, flowers, fruits and seeds. In a preferred embodiment, seeds (or other reproductive units, if the plant is not seed-bearing) of the transgenic plants produced by the methods of the invention are provided.

The plants grown from the aforementioned seeds or other reproductive units are used in crosses and selection methods to transfer the gene(s) of interest into other genotypes, cultivars, varieties and the like. Through breeding and selection, a great variety of plants can be produced that carry and express a gene or genes with the requisite characteristics.

Transgenic plants expressing one or more of the desaturase genes mentioned above, and/or overexpressing a lipase or lipoxygenase, can be generated using standard plant transformation methods known to those skilled in the art. These include, but are not limited to, Agrobacterium vectors, PEG treatment of protoplasts, biolistic DNA delivery, UV laser microbeam, gemini virus vectors, calcium phosphate treatment of protoplasts, electroporation of isolated protoplasts, agitation of cell suspensions with microbeads coated with the transforming DNA, direct DNA uptake, liposome-mediated DNA uptake, and the like. Such methods have been published in the art. See, e.g., *Methods for Plant Molecular Biology* (Weissbach & Weissbach, eds., 1988); *Methods in Plant Molecular Biology* (Schuler & Zielinski, eds., 1989); *Plant Molecular Biology Manual* (Gelvin, Schilperoort, Verma, eds., 1993); and *Methods in Plant Molecular Biology-A Laboratory Manual* (Maliga, Klessig, Cashmore, Gruissem & Varner, eds., 1994).

The method of transformation depends upon the plant to be transformed. The biolistic DNA delivery method is useful for nuclear transformation. In another embodiment of the invention, Agrobacterium vectors are used to advantage for efficient transformation of plant nuclei.

In a preferred embodiment, the gene is introduced into plant nuclei in Agrobacterium binary vectors. Such vectors include, but are not limited to, BIN19 (Bevan, 1984) and derivatives thereof, the pBI vector series (Jefferson et al., 1987), and binary vectors pGA482 and pGA492 (An, 1986).

DNA constructs for transforming a selected plant comprise a coding sequence of interest operably linked to appropriate 5' (e.g., promoters and translational regulatory sequences) and 3' regulatory sequences (e.g., terminators). In a preferred embodiment, the coding region is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase (NOS) and octopine synthase (OCS) promoters.

Transgenic plants expressing a desaturase gene under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g. hydroxyproline rich cell wall protein genes), chemically-inducible gene promoters (e.g., nitrate reductase genes, gluconase genes, chitinase genes, etc.) and dark-inducible gene promoters (e.g., asparagine synthetase gene) to name a few.

Tissue specific and development-specific promoters are also contemplated for use in the present invention. Examples of these included, but are not limited to: the ribulose bisphosphate carboxylase (RuBisCo) small subunit gene promoters or chlorophyll a/b binding protein (CAB) gene promoters for expression in photosynthetic tissue; the various seed storage protein gene promoters for expression in seeds; and the root-specific glutamine synthetase gene promoters where expression in roots is desired.

The coding region is also operably linked to an appropriate 3' regulatory sequence. In a preferred embodiment, the nopaline synthetase polyadenylation region (NOS) is used. Other useful 3' regulatory regions include, but are not limited to the octopine (OCS) polyadenylation region.

Using an Agrobacterium binary vector system for transformation, the selected coding region, under control of a constitutive or inducible promoter as described above, is linked to a nuclear drug resistance marker, such as kanamycin resistance. Other useful selectable marker systems include, but are not limited to: other genes that confer antibiotic resistances (e.g., resistance to hygromycin or bialaphos) or herbicide resistance (e.g., resistance to sulfonylurea, phosphinothricin, or glyphosate).

Agrobacterium-mediated transformation of plant nuclei is accomplished by the following procedure:

(1) the gene is inserted into the selected Agrobacterium binary vector;

(2) transformation is accomplished by co-cultivation of an appropriate plant tissue (such as leaf tissue in poplar) with a suspension of recombinant Agrobacterium, followed by incubation (e.g., two days) on growth medium in the absence of the drug used as the selective medium (see, e.g., Horsch et al. 1985);

(3) plant tissue is then transferred onto the selective medium to identify transformed tissue; and (4) identified transformants are regenerated to intact plants.

It should be recognized that the amount of expression, as well as the tissue specificity of expression of the transgenes in transformed plants can vary depending on the position of their insertion into the nuclear genome. Such position effects are well known in the art. For this reason, several nuclear transformants should be regenerated and tested for expression of the transgene. Transformed plants also may be screened for one or more additional properties, including altered fatty acid profiles and enhanced disease resistance.

The following examples are provided to further illustrate the invention. They are not intended to limit the invention in any way.

EXAMPLE 1

Expression of the Yeast Delta-9 Desaturase Gene in Tomato Enhances its Resistance to Powdery Mildew The experimental results set forth in this example demonstrate that increases in unsaturated fatty acids in transgenic tomato plants confers protection against the fungal pathogen *Erysiphe polygoni*, the causal agent of powdery mildew disease. This system is exemplified because no natural genetic resistance to the disease has been reported and the symptoms of the disease could be evaluated visually. Resistance to the fungal pathogen *Phytophthora capsicci* is also demonstrated.

Materials and Methods

Transgenic Plants

An open pollinated tomato (*Lycopersicon esculentum*) line PSR55809 was used. Transformation of tomato was carried out with cotyledon segments (Wang et al., 1996, J. Agric. Food Chem. 44: 3399–3402). *Agrobacterium tumefaciens* LBA 4404 containing the yeast Δ-9 desaturase and NPTII gene sequence driven by CaMV 35S promoters (Polashock et al., 1992, Plant Physiol. 140: 894–901) was used to infect tomato cotyledon segments. Kanamycin resistant plantlets regenerated were subjected to fatty acid analysis and Southern blotting (Shanklin & Somerville, 1991, Proc. Natl. Acad. Sci. USA 88: 2510–2514). Southern blot positive plants with high levels of palmitoleic acid were selected, multiplied in vitro and transplanted to the greenhouse. Routine greenhouse plant maintenance was implemented. Plants multiplied from the initial starting seedlings without being subjected to transformation were used as control plants. For disease resistance evaluation, two transgenic lines, T5 and T4, with moderate and high amounts of palmitoleic acid, respectively, and control plants were used.

Fatty Acid Analysis

Total fatty acid analysis was carried out according to Browse et al. (Anal. Biochem. 152: 141–145, 1986) with minor modification. Seven day old leaves were harvested and cut into small pieces. One mL of 1 M methanol hydrochloride was added to 100 mg of leaf tissue. The mixture was heated at 80° C. for 90 minutes. Hexane phase containing fatty acid methyl esters (FAME) was directly taken out for GC injection. The gas chromatograph HP 5890A was equipped a with flame ionization detector and Shimadzu CR501 integrator. A packed column (Supelco 10% SP-2330 with 100/120 chromosorb wax) was used. The injector temperature was 240° C., the detector temperature 250° C., the column temperature started from 170° C. and ended at 200° C. with a rise rate of 3° C./min. Fatty acid methyl ester peaks were identified with authentic standards from Sigma Chemical Co (St. Louis, Mo.).

Powdery Mildew Inoculation and Assessment

A small population of tomato plants infected with powdery mildew was maintained separately and used as the source of inoculum. Conidia from these plants were used to infect six-week old healthy control and transgenic plants. Plant leaves infected with conidia of *Erysiphe polygoni* were excised and shaken above the top of the test plants to allow conidia to fall onto the healthy leaves (Fletcher & Smewin, 1988, Plant Pathol. 37: 594–598). The temperature of the greenhouse was maintained at 25 to 30° C. and the humidity at above 70%. The percentage of leaf area of the inoculated plants covered by conidia or necrotic lesions was recorded.

Inoculation of *Phytophthora capsicci*

Plants propagated from cuttings were used for inoculation. *Phytophthora capsicci* Leonian was isolated from pumpkin and cultured and maintained on V8 agar medium in darkness. The culture was transferred to light for sporulation. Cytospores were collected by brushing and the suspended in distilled water for 1.5 hours to release the zoospores. Zoospore suspension at a concentration of approximately 105/mL was sprayed on the leaf and stem surface until dripping. The inoculated plants were covered with plastic film for 24 hours to keep the humidity high. Symptoms of disease were visually examined daily.

Germination of Spores of Powdery Mildew

The effect of fatty acids on the germination of *E. polygoni* spores and germ tube growth was evaluated by germinating the spores in the presence of various fatty acids. Recently colonized leaves from control plants were flicked over petri dishes containing 0.7% agar and selective fatty acid. Attempts were made to allow conidia to distribute evenly on the agar surface. The petri dishes were then incubated at 25° C. in the dark for 12 hr. Rates of germination were determined with the aid of a microscope and recorded at the end of 12 h.

Lipid Peroxidation Assay

Production of lipid peroxides was measured using the thiobarbituric acid test for malondialdehyde method of Dhindsa et al. (J. Exp. Bot. 32: 93–101, 1981). Leaf tissue was extracted with 20% trichloroacetic acid containing 0.5% thiobarbituric acid and incubated at 95° C. for 30 min. The extract was then cooled immediately in an ice-bath and centrifuged for 10 min at 10,000 g. The absorbance of the supernatant was measured at 530 nm for the peroxidation product and adjusted by subtracting the absorbance at 600 nm for the nonspecific background. The levels of peroxidation were expressed as MDA equivalent calculated by using its extinction coefficient of 155 mM$^{-1}$ cm$^{-1}$.

Results

Fatty Acids in Leaves

Fatty acids of leaves of control and transgenic plants T4 and T5 were analyzed. Leaves from individual plants of the same genotype produced similar results with no significant differences (data not shown). In contrast, leaves from different genotypes, namely, control and transgenic plants T4 and T5, possessed different levels of fatty acids (FIG. 1). Fatty acids 16:1, and 16:2 were barely detectable. No 16:3 was detected in either control or transgenic leaves. Compared to the control, the transgenic plants were found to possess higher 16:1, 16:2 and 18:1 but lower 16:0, 18:0, and 18:3 fatty acids. The increases in 16:1, 16:2, and 18:1 were sharper for T4 than for T5; T4 had approximately twice the amounts of 16:1, 16:2 and 18:1 than T5. On a percentage basis, the increases in 16:1, and 16:2 were greatest, from 800% or more over non-transformed plants.

Resistance to Powdery Mildew

Figure 2B:
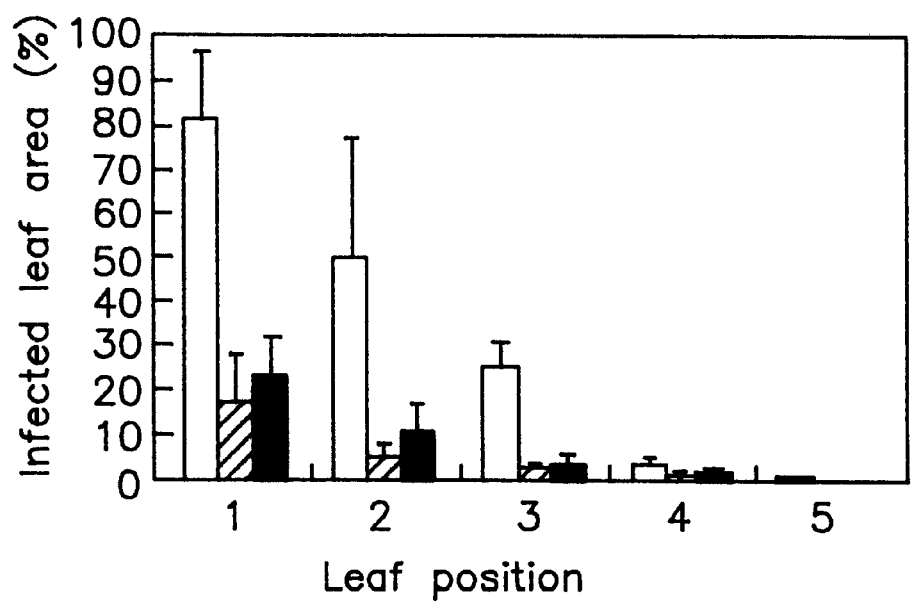
Figure 2C:
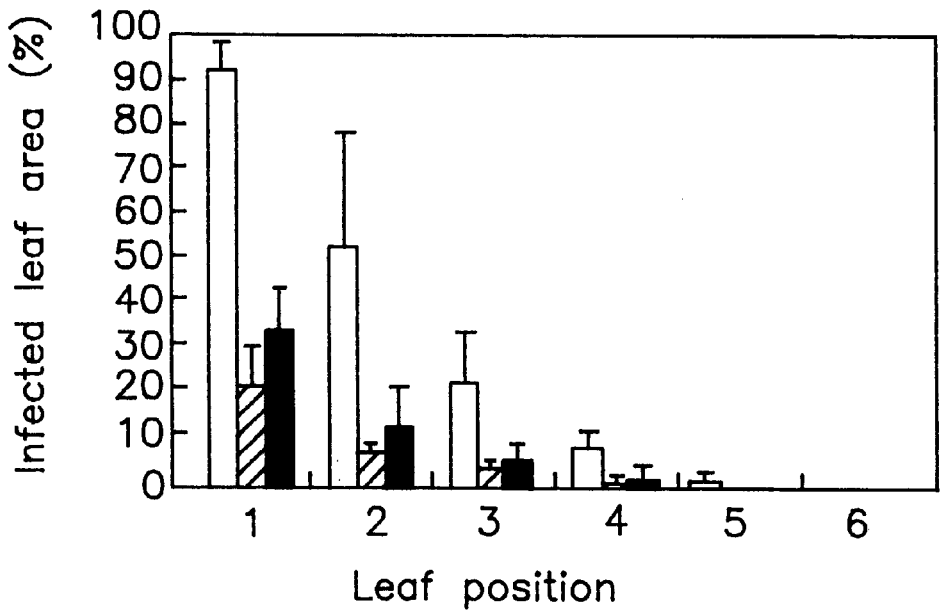
Figure 2D:
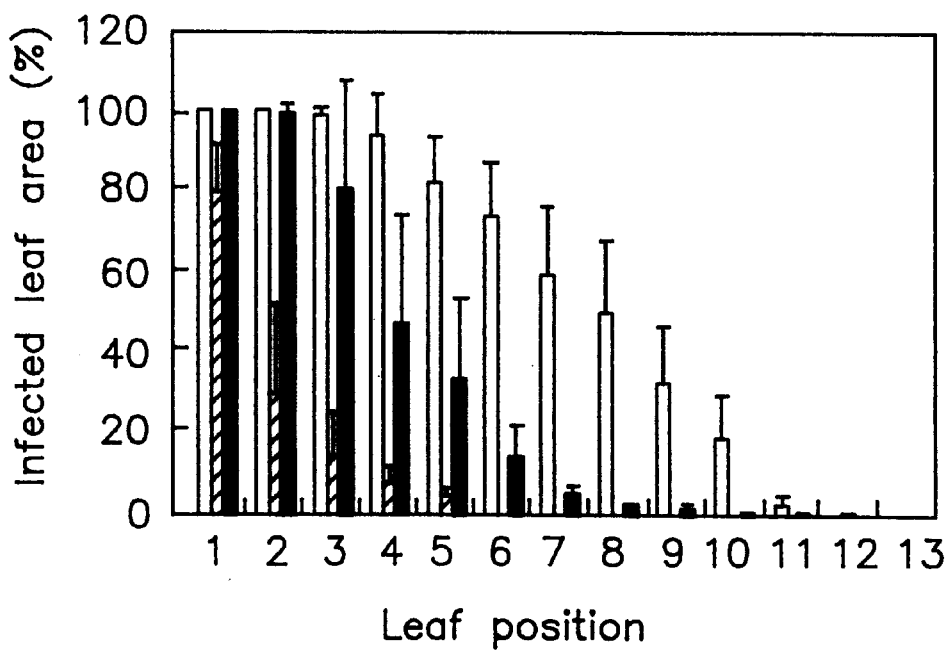

One week after the inoculation, whitish powdery spots, an indication of powdery mildew, appeared on the older leaves of both the control and transgenic plants. The colonies were found mostly on the upper surface of the leaves but a few also appeared on the lower surface and on the petioles and stems. The spots on control plants enlarged daily and often coalesced with nearby spots. In two weeks, approximately 80% of the oldest leaves were covered with fungal colonies (FIGS. 2a, 2b, and 2d). At this time those leaves started to discolor and became necrotic. As the plant grew the infection appeared on the younger leaves.

Figure 3A:
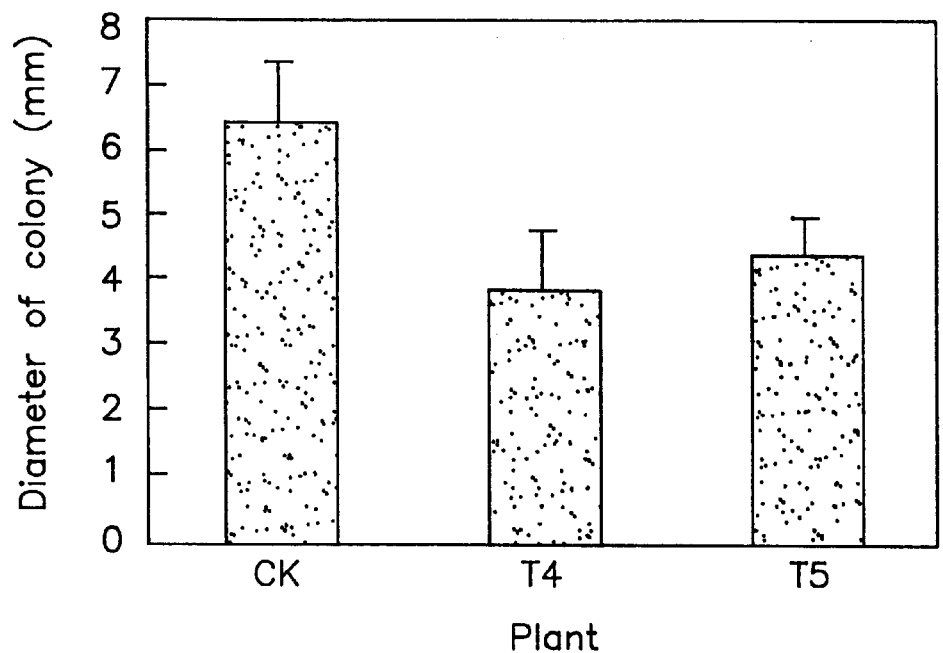
Figure 3B:
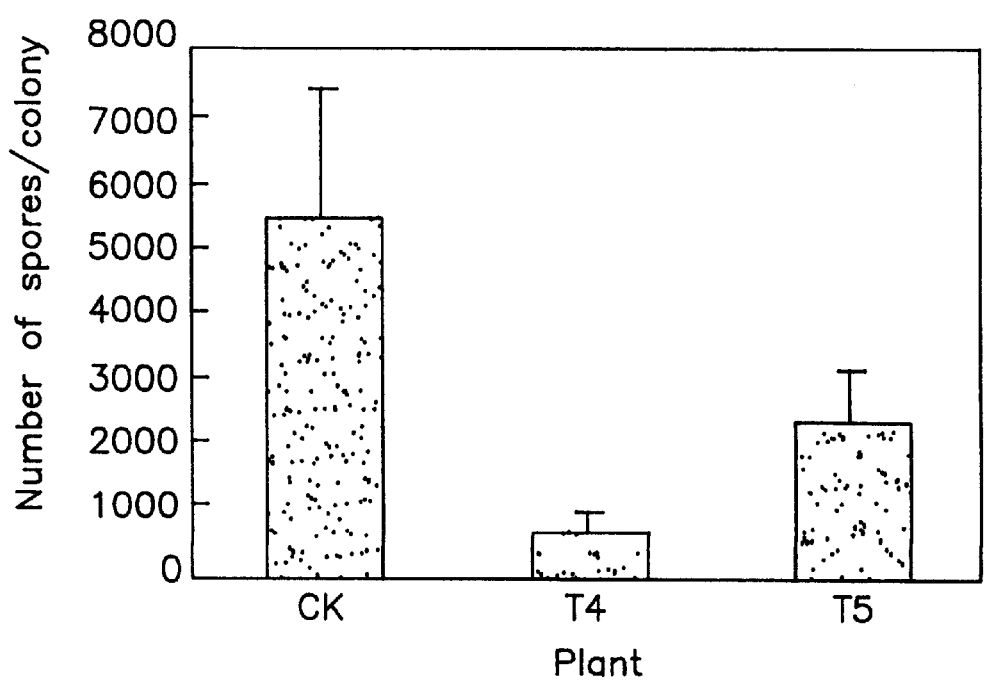
Figure 4A:
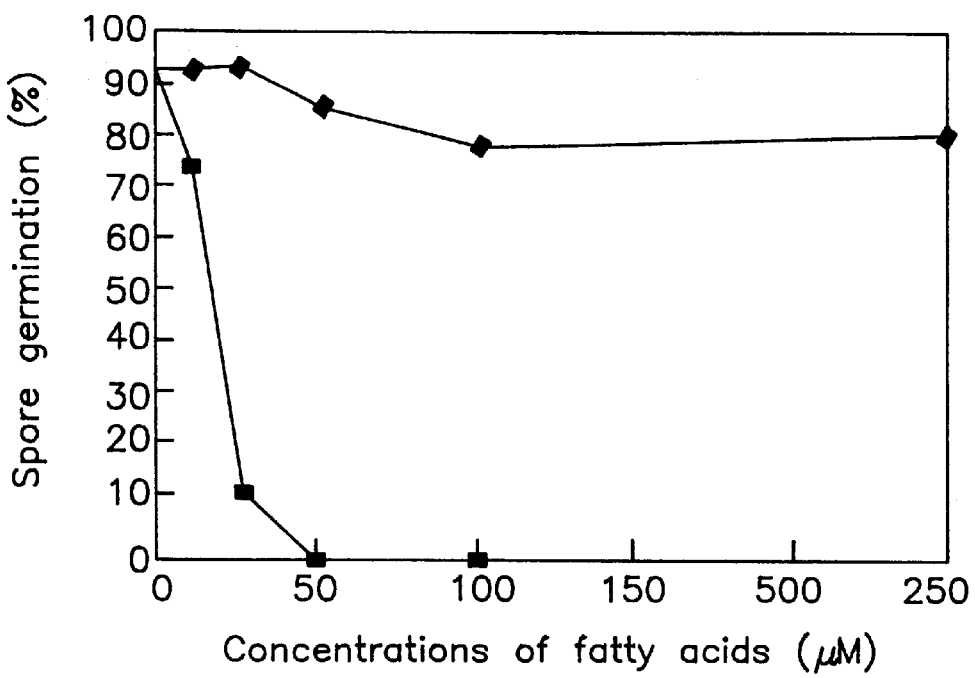

The pattern of infection was that the older the leaves the more severe the infection. Although powdery mildew colonies also appeared on T5 transgenic plants, the number of colonies were fewer (FIGS. 2a, 2b, 2c, and 2d) and the average size of the colonies was smaller (FIG. 4a). T4 plants had even fewer colonies and smaller colony sizes (FIGS. 2 and 3a). The average number of spores per colony was also found to differ among the three genotypes (FIG. 3b). The control had the highest, T5 the intermediate and T4 the lowest number of spores per colony. The average number of spores of the T4 colonies was only approximately one tenth of that of the control colonies.

Effects of Fatty Acids on Spore Germination and Germ Tube Growth

Figure 4B:
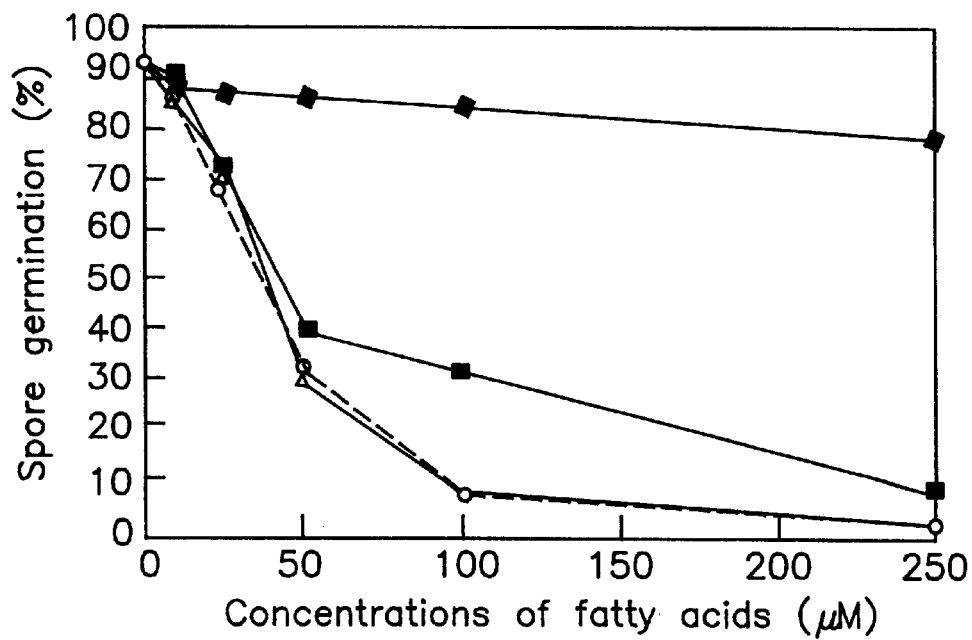

Spores of *E. polygoni* germinated readily in water and the germination was significantly inhibited by the presence of unsaturated fatty acids, but much less so by the saturated fatty acids. The fatty acid 16:1 was most inhibitory; at the concentration of 25 μM, spore germination was reduced from 93 to 12%. By comparison, over 70% of the spores germinated in the presence of 25 μM of 18:1, 18:2, and 18:3 fatty acids (FIGS. 4a and 4b). Also, the presence of 25 μM 16:1 fatty acid caused the spores to shrivel. The effect of 16:2 was not tested. Growth of germ tubes was inhibited by the presence of fatty acids; 16:0 caused a moderate reduction and 16:1 caused a much more severe reduction in germ tube elongation (FIG. 5).

Levels of Peroxides

Plant T4 was found to possess significantly higher levels of peroxides than the non-transformed control plants (FIG. 6). By contrast, the levels of peroxide of the control and T5 were not significantly different. However, when the plants were inoculated with *E. polygoni*, both T4 and T5 were found to have significantly higher levels of peroxides than the non-transformed plant. It was also noted that inoculation with *E. polygoni* led to elevated levels of peroxides in all plants measured using the thiobarbituric acid method (FIG. 6).

EXAMPLE 2

Expression of the Yeast Delta-9 Desaturase Gene in Tomato Enhances its Resistance to Tobacco Mosaic Virus The resistance of Δ-9 desaturase transgenic tomatoes to a common strain of tobacco mosaic virus (TMV) was examined. Seeds from the F1 generation of control plants and T5 transgenic plants (Example 1) were used. The Δ-9 desaturase gene segregates in T5 F1 progeny. Plants with higher (16:1/16:0 ratio≧1.2) or lower (16:1/16:0 ratio≦0.9) levels of palmitoleic acid were designated "High" and "Low", respectively.

Two week old seedlings grown in a growth chamber at 25° C. with 16 hour light period were mechanically inoculated with TMV at a concentration of 1 μg/L. The experiment was done with 15 plants in the control group and 12 plants in each of the "Low" and "High" groups.

Four weeks after inoculation, TMV infection severity was recorded in a scale of 0, 1, 2 and 3 (0=no symptoms; 1=slight mosaic on only one or two top young leaves; 2=moderate mosaic and twisting on most of leaves; 3=severe stunting of growth and deformation of leaves).

The presence of increased amounts of palmitoleic acid correlated with enhanced resistance to TMV infection. Four weeks after inoculation, control plants showed disease symptoms (disease index of 2), while the "Low" transgenic plants showed slight symptoms (disease index of 1) and the "High" transgenic plants showed almost no symptoms (disease index 0.3).

EXAMPLE 3

Expression of the Yeast Delta-9 Desaturase Gene in Eggplant Enhances its Resistance to *Verticillium dahliae*

Verticillium wilt, caused by *Verticillium dahliae* Kleb., is a major disease of eggplant (*Solannum melongena* L.). Currently, no cultivars are completely immune to Verticillium wilt, and disease management includes: fumigation, rotations, ammoniacal nitrogen application, and biological control. Soil fumigation, could reduce disease severity in fields efficiently, however, it may cause adverse environmental problems. The other kinds of management are not effective enough to control the disease in the field. Another way to control the disease is by using interspecific hybrids, but incompatibility and low yield restrict its application.

The experimental results set forth in this example demonstrate that increases in unsaturated fatty acids in transgenic eggplants transformed with the yeast Δ-9 desaturase confers protection against the fungal pathogen, *Verticillium dahliae*.

Materials and Methods

Transgenic Plants

*Solanum melongena* L. cv "Hibush" were transformed and regenerated according to the method of Billings et al. (J. Amer. Soc. Hort. Sci. 122: 158–162, 1997). *Agrobacterium tumefaciens* LBA 4404 containing the yeast Δ-9 desaturase and NPTII gene sequence driven by CaMV 35S promoters (Polashock et al., 1992, Plant Physiol. 140: 894–901) was used to infect eggplant leaf segments. Surface-sterilized seeds were germinated in test tubes on half-strength Murashige-Skoog (MS) medium containing 3% sucrose, 0.6% agar. When seedlings had 8–10 leaves, leaf segments were excised and placed (abaxial side up) on shoot regeneration (SR) medium, comprising MS medium (salts and vitamins), 10 μM $N^6$ [isopentyl] adenine (2iP) and 0.1 μM thidiazuron (TDZ). After 48 hours of culture, the leaf explants were removed from the plate, incubated for 1 minute in the Agrobacterium culture, blotted of excess bacteria and placed back onto the plate for another 48 hrs. Explants were then transferred to a selection medium comprising the above SR medium supplemented with 50 μg/ml kanamycin and 125 μg/mL augmentin (Smithkline Beecham). Plant tissue was transferred to fresh selection medium every 2–3 weeks. Transgenic shoot formation was observed to occur after several weeks. When the shoots reached a height of about 0.5 cm they were transferred to tubes containing 10 ml MS medium with 5 mM indole-3-butyric acid (IBA) and 150 μg/ml augmentin. When the shoots reached 3–5 cm with three leaves and multiple roots, the plantlets were dipped in Hormodin #1 and placed in a potting mix in the greenhouse. Kanamycin resistant plantlets regenerated were subjected to fatty acid analysis and Southern blotting (Shanklin & Somerville, 1991, Proc. Natl. Acad. Sci. USA 88: 2510–2514). Southern blot positive plants with high levels of palmitoleic acid were selected, multiplied in vitro and transplanted to the greenhouse. Routine greenhouse plant maintenance was implemented. Plants multiplied from the initial starting seedlings without being subjected to transformation were used as control plants.

Evaluation of Disease Resistance

The *Verticillium dahliae* was cultured in potato dextrose broth (PDB) and shaken at room temperature (25° C.) for one week. The conidia were collected by filtering the culture with two layers of microcloth. Hybrid eggplants at 5-leaf stage were inoculated with conidial suspension at a concentration of $3 \times 10^6$, using a stem injection method. Wilt indices were recorded 3 days after inoculation using the Horsfall-Barratt disease grading system (O'Brien, Plant Disease 67: 763–764, 1983), in which 1=plant dead and 10=no symptom. Because all the 10 transgenic plants with high 16:1 (d3, d4, d5, d8, d9, d11, d16, d17, d18, d20) were female sterile, we used transgenic plants as male and crossed with female controls. The hybrid seeds were used to evaluate disease resistance; at the 3-leaf stage, fatty acid profiles of seedlings were determined. Because all hybrid progenies with high 16:1 level showed similar resistance to *Verticillium dahliae*, we used only progenies of control X D5 in the subsequent experiments, and only those seedlings with high 16:1 were referred to as transgenic plants. Twelve plants in each group were evaluated. All samples for the experiments reported were the third leaves from the top, and experiments were repeated three times.

In vitro Inhibition of Verticillium Growth By Fatty Acid

A thin layer potato dextrose agar (PDA) medium containing different concentrations of fatty acids was coated on individual cover slides. Five micrograms of conidial suspension ($3 \times 10^6$/ml) was added on the center of the slide, then cultured at room temperature in petri dishes with wet filter paper to retain moisture.

Fatty Acid Analysis

Two grams and 0.2 grams of leaf tissue were used for free fatty acid and total fatty acid analysis, respectively. Free fatty acid purification was essentially by the method of Coconi (Plant Physiol. 111: 797–803, 1996). After two solid extractions, free fatty acids were isolated by one-dimensional TLC on silica gel G with development in 17.5:82.5:1 (ether:light petrol ether:formic acid) according to Kates (Techniques of Lipidology, Elsevier Science, Amsterdam, 1986, p 484). Pure 16:1 fatty acid (Sigma Chemical Co.) was used in the same TLC plate for localizing free fatty acid position. Lipids were visualized by iodine vapor. The gel containing free fatty acid was scraped. Total fatty acids (using leaf tissue directly) and free fatty acids were methylated in the presence of 17:0 fatty acid as an internal standard. Quantification was by gas chromatography as described by Wang (J. Food Agri. Chem. 44: 3399, 1996).

Phospholipase $A_2$ Extraction and Assay

Extraction of phospholipase A2 from microsomes and subsequent activity assays followed the method of Lee, et al. (Phys. Molec. Pl. Pathol. 41: 283–294, 1992), using 1.5 KBq 2-[1-$^{14}$C] linoleoyl phosphotidylcholine and 50 μM cold phosphatidylcholine as substrate. Two grams leaf tissue were used.

Lipoxygenase Extraction and Assay

The enzyme extraction and activity assay followed the method of Avdiushko et al. (Phys. Molec. Plant Pathol. 42: 83–95, 1993) with minor modifications. 0.5 grams of leaf was used for each sample and pH 7.6 buffer was used, as a result of preliminary trials.

Lipid Peroxide Determination

Lipid peroxide was determined spectrophotometrically (Mishra & Singhal, Plant Physiol. 98: 1–6, 1992) by measuring MDA formation in the thiobarbituric acid method.

Results

Fatty Acid Profiles of Transgenic and Control Plants

Out of 14 regenerants of the transformation described above, 10 plants displayed elevated 16:1 fatty acid. Because these high 16:1 plants displayed similar fatty acid profiles, the average fatty acid profiles of transgenic and non-transgenic plants are shown below in Table 1.

TABLE 1

Total fatty acid composition in control and transgenic leaves
(μg/gfw leaf tissue)

| | 16:0 | 16:1 | 16:2 | 18:0 | 18:1 | 18:2 | 18:3 | Total FA | Total USFA |
|---|---|---|---|---|---|---|---|---|---|
| transgenic | 1286 ± 16 | 1705 ± 18 | 189 ± 5 | 325 ± 7 | 560 ± 8 | 1759 ± 21 | 2823 ± 29 | 8647 ± 117 | 7036 ± 103 |
| control | 1699 ± 20 | 139 ± 4 | 63 ± 5 | 522 ± 11 | 495 ± 6 | 2281 ± 19 | 3591 ± 41 | 8792 ± 89 | 6571 ± 74 |

FA = fatty acids, USFA = unsaturated fatty acids.

The transgenic plants showed different fatty acid profiles compared to non-transgenic controls. The most significant differences were: (1) transgenic plants showed elevated 16:1 and oleic acid (18:1), especially 16:1, which was increased by about 10-fold; (2) transgenic plants showed lower amounts of linoleic and linolenic acids; (3) transgenic plants possessed more total unsaturated fatty acids (10% more) than control plants with concomitantly less saturated fatty acids being produced in transgenic plants, especially palmitic acid (16:0), which is direct precursor of 16:1; and (4) there was no significant difference in total fatty acid between control and transgenic plants. These results demonstrate that the yeast Δ-9 desaturase gene expresses a functional desaturase that is effective in the eggplant fatty acid synthesis system, and predominantly desaturates 16:0 to 16:1. That the transgenic desaturase prefers 16:0 as a substrate differs from its counterpart in plant, which mainly produces 18:1, using stearic acid (18:0) as a substrate.

Enhanced Resistance to *Verticillium dahliae*

Both control and transgenic plants could be infected by Verticillium, and the symptoms were similar. However, infection of transgenic plants was retarded as shown in FIG. 7. The control plants began to show symptoms 5 days after inoculation, whereas the transgenic plants began to show symptoms on the 7th day. The disease-severity score of transgenic plant was always higher than that of control plants. These results demonstrate that expression of the yeast desaturase gene provide protection for eggplants against Verticillium. In Example 1, transgenic tomatoes were found to be completely resistant to powdery mildew, and partially resistant to *Phytophthora capsici*. Thus, expression of the yeast Δ-9 desaturase gene contributes to wide-spectrum disease resistance.

In vitro Inhibition of Verticillium Growth By Fatty Acids

To determine possible mechanisms of enhanced disease resistance conferred by transformation with the yeast Δ-9 desaturase, we tested the effects of various fatty acids on Verticillium growth in vitro. As shown in FIG. 8, monounsaturated fatty acids had highest inhibitory effect on Verticillium growth, especially 16:1, which began to inhibit at 200 μM. Saturated and polyunsaturated fatty acids had little effect, and only at extremely high concentrations. Transgenic plants expressing the yeast Δ-9 desaturase possess increased monounsaturated fatty acids, which could directly contribute to resistance to Verticillium, based on their inhibitory effect in vitro.

Induction of Lipase Activity By Verticillium

Free fatty acids are immediately incorporated into phospholipids in the plant cell. Phospholipid can be digested by phospholipase $A_2$ and other lipases into lisophospholipid and unsaturated free fatty acids. Changes in phospholipid, lisophospholipid and free fatty acids are associated with wounding, pathogen attack and other stresses. These molecules are believed to act as signals in plant defensive signal transduction systems (Lee et al., 1992, supra). FIG. 9 shows a time course of phospholipase $A_2$ activity in transgenic and control plants after inoculation with Verticillium. The transgenic plants showed higher constitutive phospholipase $A_2$ activity than did control plants. After plants were inoculated with Verticillium, the phospholipase $A_2$ activities were stimulated in both control and transgenic plants on 3rd day after inoculation, and began to decline from the 6th day. During that time, the phospholipase $A_2$ activity in transgenic plants showed a similar pattern of activity as did the control plants, but the transgenic plants showed higher activity overall. The induction of phospholipase $A_2$ preceded the free fatty acid surge associated with Verticillium inoculation (see below), at least with respect to free unsaturated fatty acids, which are the product of phospholipase $A_2$.

Free Fatty Acid Burst Correlates With the Increase in Phospholipase A2 Activity

Although the in vitro study described above showed that 16:1 and 18:1 could inhibit Verticillium growth, the free unsaturated fatty acid content in plant cells is generally not high enough to provide disease resistance. To evaluate the potential role of endogenous free fatty acids on Verticillium resistance, we measured the free fatty acid content of the plant cells after inoculation. We measured 16:0, 16:1, 16:2, 18:0, 18:1, 18:2 and 18:3; FIG. 10 shows the 16:0 and 16:1 results. In the healthy control plants, the major varieties of free fatty acid were the saturated fatty acids, e.g., 16:0 and 18:0. As reported in other plant materials, the total free fatty acid content is about 1 percent of total fatty acid. In contrast to the control plants, the healthy transgenic plants possessed a large amount of free 16:1, in addition to the two saturated fatty acids. After inoculation with Verticillium, the inoculated plants displayed a burst of free fatty acid from day 3 to day 4, which then decreased. It was noted that free unsaturated fatty acids increased more than saturated fatty acids. In addition, transgenic and control plants showed different profiles of changes in their respective free fatty acids. First, free fatty acids in the transgenic plants were elevated more than in the control plants. During day 3 and day 4, free fatty acids in transgenic plants increased by about 3 fold, whereas in controls the increase was about 2 fold. Second, the transgenic plants possessed a comparatively large amount of free 16:1. In fact, on the 3rd and 4th day, the 16:1 content reached a concentration of about 250 μM, which is the concentration at which 16:1 was able to inhibit Verticillium growth in vitro. Thus, high free 16:1 in transgenic plants could inhibit Verticillium infection directly, as one mechanism of disease resistance.

The free fatty acid burst coincided with the increase in phospholipase $A_2$ activity. In both control and transgenic plants, phospholipase $A_2$ increased by two-fold from the 3rd day after inoculation, and sustained at high level for two more days, then decreased. Moreover, unsaturated fatty acids increased more than saturated ones. The results strongly indicate that phospholipase $A_2$ is involved in the defensive reaction observed in the inoculated eggplants. Other kinds of lipases could also participate in this defense response, inasmuch as large amount of saturated fatty acids were released as well.

Induction of Lipoxygenase Activity

Lipoxygenases play important roles in plant responses to disease infection and wounding. In the experiments described above, lipoxygenase activity began to increase 4 days after inoculation and declined from 6th day (FIG. 11). The surge of lipoxygenase activity was one day behind the free fatty acid increase. Similarly, transgenic plants showed higher lipoxygenase activity than did control plants. These results indicate that lipoxygenase activities were induced by their substrates, which are free fatty acids.

Lipid Peroxides

Lipid peroxides, which are the products of lipoxygenases, could be inhibitory to pathogen growth or could function as a defense response signaling molecule. Uninoculated transgenic plants contained more lipid peroxide than did control plants (FIG. 12). From the 4th day after inoculation, increased amounts of lipid peroxides were evident. Until the 6th day, lipid peroxide content in transgenic plants was higher than in control plants. After that, presumably because the control plants were more severely damaged, more peroxides were produced in those plants. In addition to direct inhibition of the pathogen by 16:1, this higher content of lipid peroxides at an early stage of infection could also contribute to disease resistance in transgenic plants.

Total Fatty Acid Alterations

The Verticillium infection caused fatty acid oxidation. The total fatty acid content in inoculated plants was significantly lower than in water treated plants by the 7th day after inoculation. The decline of unsaturated fatty acids was more significant than that of saturated ones, in terms of both absolute amount and percentage. Corresponding to lipid peroxides, on the 4th day following inoculation, more unsaturated fatty acids were oxidized in transgenic plants, but on the 7th day, unsaturated fatty acids were decreased more in control plants, presumably due to more damage in the control plant tissues.

EXAMPLE 4

Change in the Fatty Acid Profiles in Cutin Monomers of Δ-9 Desaturase Transgenic Tomato, and the Effect on Resistance to Powdery Mildew Above ground plant surfaces, including those of leaf, stem, flower, and fruit are covered by a cuticle consisting of cutin, wax, and polysaccharide microfibrils. The cuticle has long been recognized to function as a physical barrier to water loss and pathogen invasion. Recently, evidence has been accumulating to indicate that components of the cuticle also play a role in signaling in pathogenesis. For example, surface wax of avocado plants susceptible to *Colletotrichum gloeosporioides*, selectively induces the germination and appresorium formation of the pathogen, whereas those from the non hosts could not induce such development. Another component of the cuticle, cutin, also has been implicated in signaling. Cutin primarily consists of polymeric esters of hydroxylated and epoxydized fatty acid monomers. It has been reported that before and during germination, conidia of *Erysiphe graminis* produces exudates containing esterases, cutinase and other extracellular hydrolytic enzymes, leading to the hydrolysis of cutin and release of cutin monomers. The presence of cutin monomers in turn stimulates germination and appresorium formation. Indeed, when cutin monomers are coated onto glass microscope slides they dramatically stimulate the appressorial germ tube differentiation in germinating *E. graminis* conidia. In addition, suppression of cutinase with inhibitors such as diisopropyl fluorophosphate (DFP), and anti-cutinase antibodies reduces the appresorium formation and pathogenicity. However, the presence of cutin monomers is not always to the advantage to the fungi. Topical spray application of cutin monomers protects leaves of a highly susceptible barley cultivar against *E. graminis* f. sp. *hordei*. The degree of protection depends on the specific monomer. Thus, evidence has been accumulating to suggest the involvement of cutin monomers in the infection and defense of certain pathogens.

If cutin monomers play a role in pathogenicity, then changes in their composition could lead to alterations in susceptibility. Cutin monomers are derived from fatty acid precursors, therefore, changes in the fatty acid profile should produce corresponding changes in the cutin monomer profile. We have observed that tomato plants transformed with the yeast Δ-9 desaturase gene possessed different fatty acid profiles (Polashok et al., 1992, supra). These plants also displayed enhanced resistance to powdery mildew, *Erysiphe polygoni* DC, a pathogen that penetrates the cuticular layer during the course of its infection (Example 1). In this example, we correlate the enhanced resistance of the plants transformed with the yeast Δ-9 desaturase gene with the changes in cutin composition.

Materials and Methods

Transgenic Plants

Transgenic tomato plants were generated as described in the previous examples. Two transgenic lines, T4 and T5, with moderate and high amounts of 9-hexadecenoic acid respectively, and control plants were propagated vegetatively by cuttings and used in this example.

Fatty Acids

Fatty acids extraction and analysis were carried out as described in the previous examples.

Cutin Monomers

Cutin monomers were prepared according to the method of Walton and Kolattukudy (1972) with slight modification. Epicarp peeled from red fruits was treated with oxalic acid/ammonium oxalate (0.4%:1.6%) solution at 48° C. on a shaker set at 120 rpm for 24 hours, and rinsed thoroughly in deionized water. The sheets were then transferred to a Pectolyase Y23 (Seishin Pharmaceutical, Tokyo, Japan)/Cellulysin (Calbiochem) (0.5%:0.5%) solution at 34° C. for 24 hours, followed by rinsing with deionized water and incubation in chloroform for 24 hours. Leaf cutin sheets were prepared from 1-cm square leaf discs and the discs were directly subjected to enzyme digestion. Cutin sheets were re-fluxed in 14% BF 3 in methanol to make the methyl esters of the acid monomers and extracted with methylene chloride. The extract was dried over anhydrous sodium sulfate, and then decanted, evaporated to dryness under $N_2$. The dried extract was redissolved in ethyl acetate, derivatized to the TMSi ethers with 200 μl bis(trimethylsilyl) trifluoroacetamide containing 1% trimethylchlorosilane (Sigma Chemicals) at 75° C. for 30 minutes. Derivatized cutin monomers were separated and identified with a HP 5890 GC equipped with a DB 1701 capillary column (30 m, 0.25-m ID, 0.25-m film thickness, J and W Scientific, Folsom, Calif.) and coupled to a HP-5970 mass selective detector. The temperature program was from 140° C. to 260° C. at a rate of 5° C./min after 3 minutes, and kept at final temperature for 30 minutes. Peaks were identified by referring to a Wiley mass spectral library or to published data.

Spore Germination

Spores were germinated on cutin sheets or on phytagel. For the former, cutin sheets were placed in a petri dish and surround with water droplets. Tomato leaf infected with *E. polygoni* was flicked over the cutin sheet. Spores were also germinated on 0.7% phytagel containing cutin monomers prepared from fruits. Attempts were made to allow the conidia to distribute evenly on the cutin sheet or on phytagel. The petri dishes continuing the spores were incubated at 25° C. in the dark for 12 hours. Percentage of germination was determined with the aid of a microscope.

Results

Fatty Acids

The fatty acid composition of the leaves from plants transformed with the yeast Δ-9 desaturase gene, T4 and T5, were different from that of the control. The leaves from transgenic plants had higher 16:1, 16:2, and 18:1 but lower 16:0, 18:0, and 18:3 fatty acids. The increases in 16:1, 16:2, and 18:1 were greater for T4 than for T5; T4 had approximately twice the amounts of 16:1, 16:2, and 18:1 than T5. T4 and T5 fruits also displayed different fatty acid profiles from that of the control fruits. Just like the T4 and T5 leaves, T4 and T5 fruits also had higher levels of 16:1, 16:2, and 18:1 and lower levels of 16:0, 18:0 and 18:3 fatty acids. However, unlike the transgenic leaves in which there was no conspicuous change in the levels of 18:2 fatty acid, T4 and T5 fruit had large amounts of this fatty acid.

Cutin Monomers

We measured cutin monomers as percentages found in the leaves of control and transgenic plants T4 and T5. On a percentage basis the most abundant monomers were 10,16-dihydroxyhexadecanoic, 10-hydroxy-octadecanedioic, and 16-methoxy-10-hydroxy-12-hexadecenoic. Together, these 3 monomers made up approximately 70% of the total monomers found in control and transgenic leaves. Plants transformed with the yeast Δ-9 desaturase gene exhibited notable changes in the relative amounts of certain monomers. There were increases in 9-hexadecenoic, 1,16-hexadecanedioic, 10,16-dihydroxyhexadecanoic, 9,16-dihydroxyhexadecanoic, and 16-hydroxy-9-hexadecenoic. The increase in 9-hexadecenoic was most dramatic; it was undetectable in control leaves but was 5.05% and 4.83% of the T4 and T5 total cutin monomers respectively. Larger number of monomers showed a decline. Most conspicuous ones were octadecanoic, 18-methoxy-9,10-epoxy-12-octadecenoic, 10-hydrooctadecanedioic, and 18-hydrooctadecanoic. It is of interest to note that the monomers that showed an increase (>10%) had 16 carbons and those that showed notable decreases had 18 carbons. The changes of monomer profiles of T4 and T5 were similar, but that of the T4 was more different from the controls than that of the T5.

The cutin monomers of tomato fruits share some similarities with those of the leaves; the two most abundant monomers, 10,16-dihydroxyhexadecanoic, and 10-hydroxyoctadecanedioic, found in leaves were also found in the fruit. These two compounds comprised over 70% of the total cutin monomers of the fruit. However, the monomers 18-hydrooctadecanoic and octadecanoic found in the leaves were not detected in the fruits. Conversely four of the monomers, viz. 16-methoxy-10-hydroxyhexadecanoic, 16-hydroxy-10-oxohexadecanoic, 18-methoxy-9,10-epoxyoctadecanoic, and 9,10,18-trihydroxyoctadecanoic acids found in the fruits were not detected in the leaves. In the leaves, there were higher levels of the unsaturated monomers 16-methoxy-10hydroxy-12-hexadecenoic acid and 18-methoxy-9,10-octadecenoic acid than in the fruits. The saturated derivatives of these compounds were present in fruit but not in leaves. The changes in monomer profiles in transgenic fruits showed some but also some differences with that of the control fruits. The monomers 9-hexadecenoic, 1,16-haxadecanedioic, and 16-hydroxy-9-hexadecenoic that showed increases in the leaves also did so in fruits. In addition, other monomers including 18-methoxy-9,10-epoxy-12-octadecenoic, hexadecanoic, and 16-hydroxy-10-oxohexadecanoic showed obvious increases. In contrast to the leaves, not all increases in fruits were with the 16-carbon monomers. Six of the monomers declined considerably in the transgenic fruits. One of them was the predominant monomer, 10,16-dihydroxyhexadecanoic. It was noted that this monomer showed a modest increase in the transgenic leaves but a noticeable decline in the transgenic fruits.

Spore Germination

Germination of spores of *E. polygoni* on cutin sheets from leaves and fruits of control and transgenic plants was examined. Compared to the germination on the control sheets, germination on T4 and T5 cutin sheets was reduced by approximately one half. No notable differences between the germination percentages on T4 and T5 cutin sheets were observed. To study whether the inhibition by the T4 and T5 cutin sheets was related to the monomers, the cutin sheets of fruits were digested and resulting monomers were incorporated into phytagel. Approximately 80% of the spores germinated on phytagel containing no cutin monomers. The presence of monomers, including the monomers from the control plant, inhibited spore germination but those from the transgenic plants were considerably more inhibitory and the T4 monomers were more inhibitory (40% germination) than were those of T5 (55% germination).

Discussion

The compositions of fatty acids of the transgenic plants T4 and T5 were changed by the expression of the yeast Δ-9 desaturase gene. Certain cutin monomers were not detectable in the leaves but were present in the fruits, and others were just the opposite. One of the monomers found only in fruits is 18-methoxy-9,10-epoxyoctadecanoic acid. This monomer also showed marked increases in T4 and T5 fruits. Marked increase in octadecanoic and octadienoic acids were found in transgenic fruits but not in leaves.

In the examples above we have described the effects of the expression of the yeast Δ-9 desaturase gene on tomato. Compared to the control plants transgenic plants with the yeast Δ-9 desaturase gene display enhanced resistance to powdery mildew (Example 1). Of the two transgenic lines, T4 and T5, the former was more resistant than the latter. Although powdery mildew does not usually infect fruit, during heavy infection colonies can be found on some red control fruits. We have not observed powdery mildew colonies on T4 or T5 fruits.

To examine whether changes in cutin compositions could play a role in the enhanced resistance of T4 and T5 plants, germination of spores of *E. polygoni* on cutin sheets was compared. Germination of spores on T4 and T5 cutin sheets was inhibited, which would support the proposition that cutin composition plays a role in determining pathogen activity. Fungal spores have been reported to secrete cutinase, which hydrolyzes cutin, upon contact with the host surface. The cutinase releases cutin monomers which in turn could increase the expression of the cutinase gene in the germinating fungal spores, allowing the production of additional cutinase to assist cuticular penetration. However, the presence of cutin monomers may not only be advantageous to the fungus. Some plants appear to use the presence of cutin monomers as a signal of pathogen attack and to initiate the defense process. Topical application of certain cutin monomers has been found to protect leaves of a highly susceptible barley cultivar against *E. graminis*. The reduction of germination of *E. polygoni* spores on the T4 and T5 cutin sheets could be the result of the release of inhibitory monomers following the inoculation. To examine this, spore germination on phytagel containing cutin monomers isolated from fruits was compared. As predicted, the presence of monomers from T4 and T5 fruits was inhibitory to germination of spores. The inhibition by the monomers from the transgenic plants indicates that the monomers were the result of the expression of the yeast Δ-9 desaturase gene.

The present invention is not limited to the embodiments described and exemplified above, but is capable of variation and modification without departure from the scope of the appended claims.

What is claimed is:

1. A method of making a pathogen-resistant plant, which comprises:

a) transforming regenerable cells of a plant with a heterologous DNA, expressible in a plant, encoding a fatty acid desaturase whose activity increases production of at least one unsaturated fatty acid;
   b) regenerating transgenic plants from the cells, and
   c) screening the transgenic plants to identify a transgenic plant which produces more unsaturated fatty acids and which is more pathogen-resistant than a corresponding untransformed plant.

2. The method of claim 1, wherein the fatty acid desaturase is a Δ-9 desaturase.

3. The method of claim 2, wherein the Δ-9 desaturase is a yeast Δ-9 desaturase.

4. The method of claim 1, wherein the unsaturated fatty acids comprise a 16:1 fatty acid.

5. The method of claim 1, wherein the plant is selected from the group consisting of tobacco, tomato and eggplant.

6. The method of claim 1, wherein the plant is tomato and the pathogen is selected from the group consisting of *Erisyphe graminis, Phytophthora capsicci, Pseudomonas syringae* and tobacco mosaic virus.

7. The method of claim 1, wherein the plant is eggplant and the pathogen is *Verticillium dahliae*.

* * * * *